United States Patent
Matsumoto et al.

(10) Patent No.: US 9,952,230 B2
(45) Date of Patent: Apr. 24, 2018

(54) METHOD OF INHIBITING NONSPECIFIC REACTION IN PIVKA-II ASSAY REAGENT

(75) Inventors: Takuji Matsumoto, Ibaraki-ken (JP); Mitsuaki Yamamoto, Chiba-ken (JP)

(73) Assignee: SEKISUI MEDICAL CO., LTD., Tokyo (JP)

(*) Notice: Subject to any disclaimer, the term of this patent is extended or adjusted under 35 U.S.C. 154(b) by 1039 days.

(21) Appl. No.: 14/116,155

(22) PCT Filed: May 23, 2012

(86) PCT No.: PCT/JP2012/063220
§ 371 (c)(1),
(2), (4) Date: Dec. 11, 2013

(87) PCT Pub. No.: WO2012/161226
PCT Pub. Date: Nov. 29, 2012

(65) Prior Publication Data
US 2014/0113387 A1    Apr. 24, 2014

(30) Foreign Application Priority Data

May 23, 2011    (JP) ................................ 2011-114776

(51) Int. Cl.
| | |
|---|---|
| *G01N 33/86* | (2006.01) |
| *G01N 33/541* | (2006.01) |
| *G01N 33/542* | (2006.01) |
| *G01N 33/82* | (2006.01) |

(52) U.S. Cl.
CPC .......... *G01N 33/86* (2013.01); *G01N 33/541* (2013.01); *G01N 33/542* (2013.01); *G01N 33/82* (2013.01)

(58) Field of Classification Search
CPC .... G01N 33/86; G01N 33/541; G01N 33/542; G01N 33/82
See application file for complete search history.

(56) References Cited

U.S. PATENT DOCUMENTS

| | | | | |
|---|---|---|---|---|
| 4,486,530 | A * | 12/1984 | David .................. | G01N 33/542 435/7.91 |
| 6,248,597 | B1 * | 6/2001 | Eda .................. | G01N 33/54346 422/52 |
| 6,624,295 | B1 * | 9/2003 | Adams .................. | C07K 16/36 536/23.53 |
| 9,133,259 | B2 * | 9/2015 | Haudenschild ...... | C07K 14/475 |
| 2011/0236884 | A1 * | 9/2011 | Jablonski ......... | G01N 33/54313 435/5 |

FOREIGN PATENT DOCUMENTS

| | | |
|---|---|---|
| JP | 5-43367 B2 | 7/1993 |
| JP | 5-249108 A | 9/1993 |
| JP | 9-249699 A | 9/1997 |
| JP | 10-123137 A | 5/1998 |
| JP | 3307422 B2 | 7/2002 |
| JP | 2003-75438 A | 3/2003 |

OTHER PUBLICATIONS

"Basic studies on determination of PIVKA-2 with TZR-110." The Journal of Clinical Laboratory Instruments and Reagents (1985), vol. 8, No. 1, pp. 88-98, Abstract.
Belle et al., "Des-gamma-carboxyprothrombin detection by immunoblotting after polyacrylamide gel affinoelectrophoresis in human plasmas," Electrophoresis (Apr. 1991), vol. 12, pp. 294-297.
Belle et al., "Production of a new monoclonal antibody specific to human des-gamma-carboxyprothrombin in the presence of calcuim ions, application to the development of a sensftive elisa-test," J. Immunoassay (1995) vol. 16, No. 2, pp. 213-229.
International Search Report dated Jul. 3, 2012, in PCT international Application No. PCT/JP2012/063220.
English translation of International Preliminary Report on Patentability and Written Opinion dated Dec. 5, 2013, in PCT International Application No. PCT/JP2012/063220.
Supplementary European Search Report dated Nov. 24, 2014, in European Patent Application No. 12789768.
Matsuzaka et al., "Relationship between vitamin K dependent coagulation factors and anticoagulants (protein C and protein S) in neonatal vitamin K deficiency," Archives of Diseases in Childhood (1993), vol. 68, pp. 297-302.
Meguro T. and K Yamamda, "A Simple and Rapid Test for PIVKA-II in Plasma," Thrombosis Research (1982), vol. 25, pp. 109-114.
European Office Action for European Application No. 12789768.4, dated Oct. 13, 2016.

* cited by examiner

*Primary Examiner* — Gary Counts
(74) *Attorney, Agent, or Firm* — Birch, Stewart, Kolasch & Birch, LLP

(57) ABSTRACT

A problem to be solved by the present invention is to inhibit a nonspecific agglutination reaction in an agglutination test using a monoclonal antibody having a property of specifically biding to PIVKA-II and a monoclonal antibody having a property of specifically biding to prothrombin as well as two types of carrier particles carrying these monoclonal antibodies. The nonspecific agglutination reaction can be inhibited by adding certain divalent metal ions to a reaction solution containing the monoclonal antibody having a property of specifically biding to PIVKA-II and the monoclonal antibody having a property of specifically biding to prothrombin as well as the two types of carrier particles carrying these monoclonal antibodies.

10 Claims, 5 Drawing Sheets

[FIG. 1]
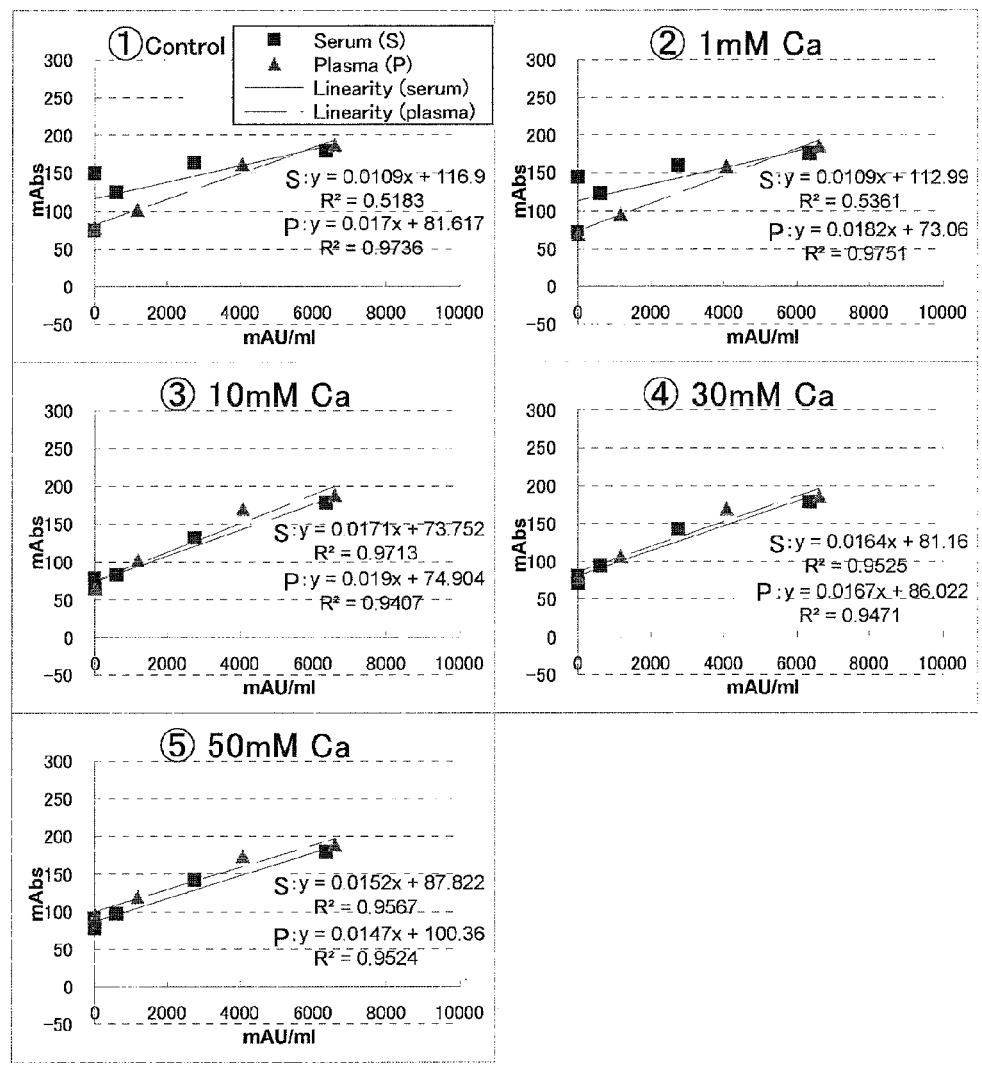

[FIG. 2]
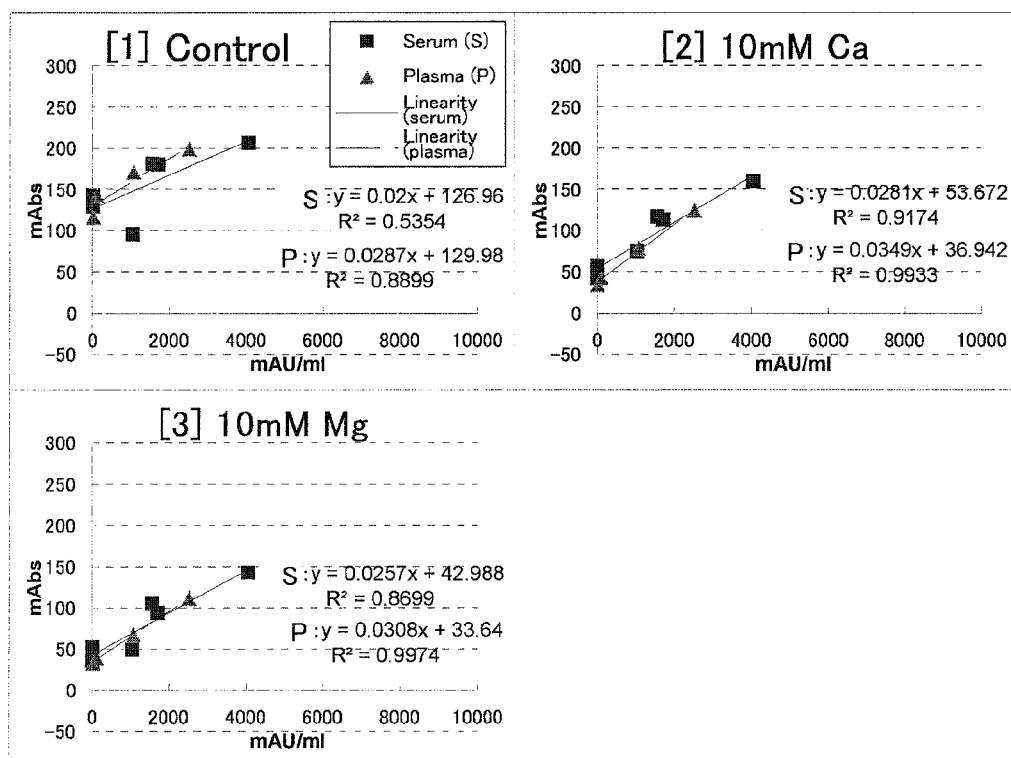

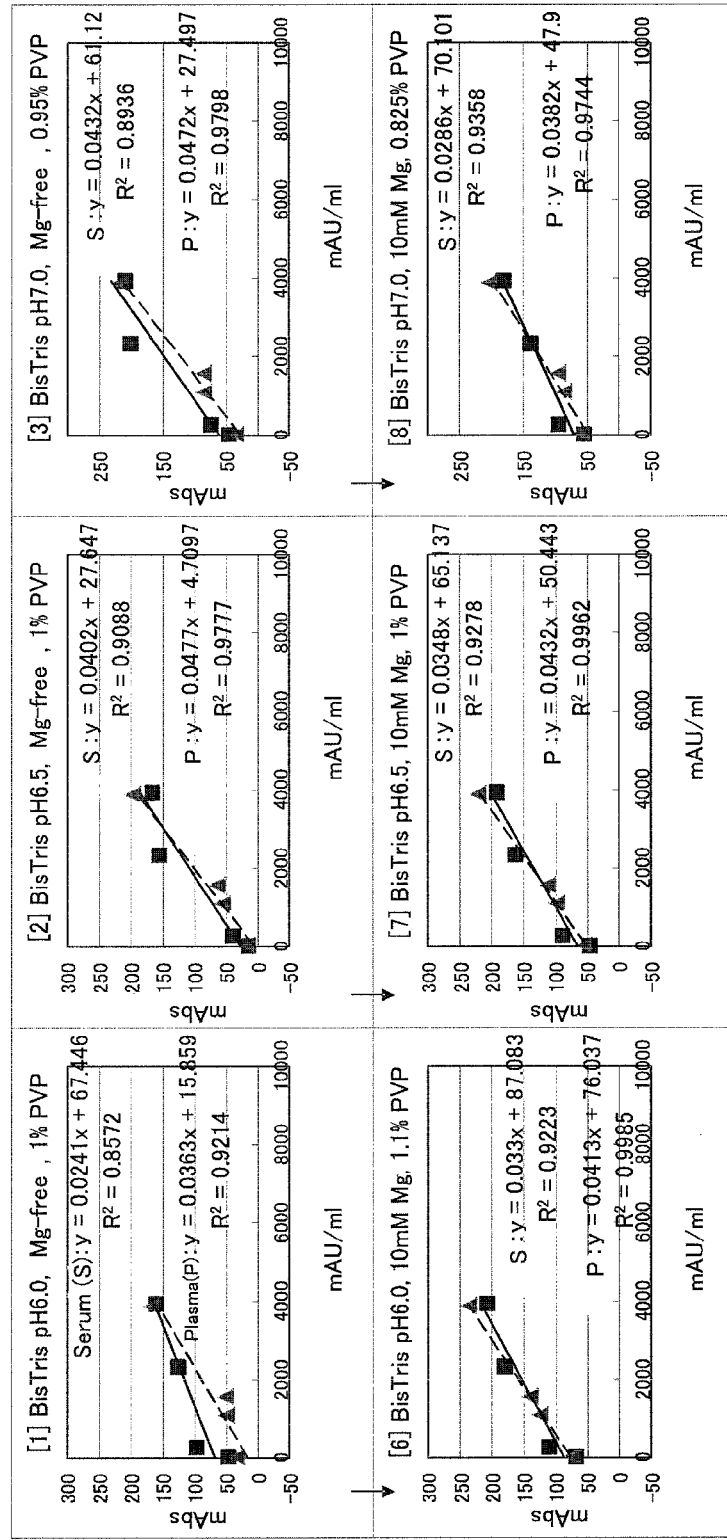
[FIG. 3-1]

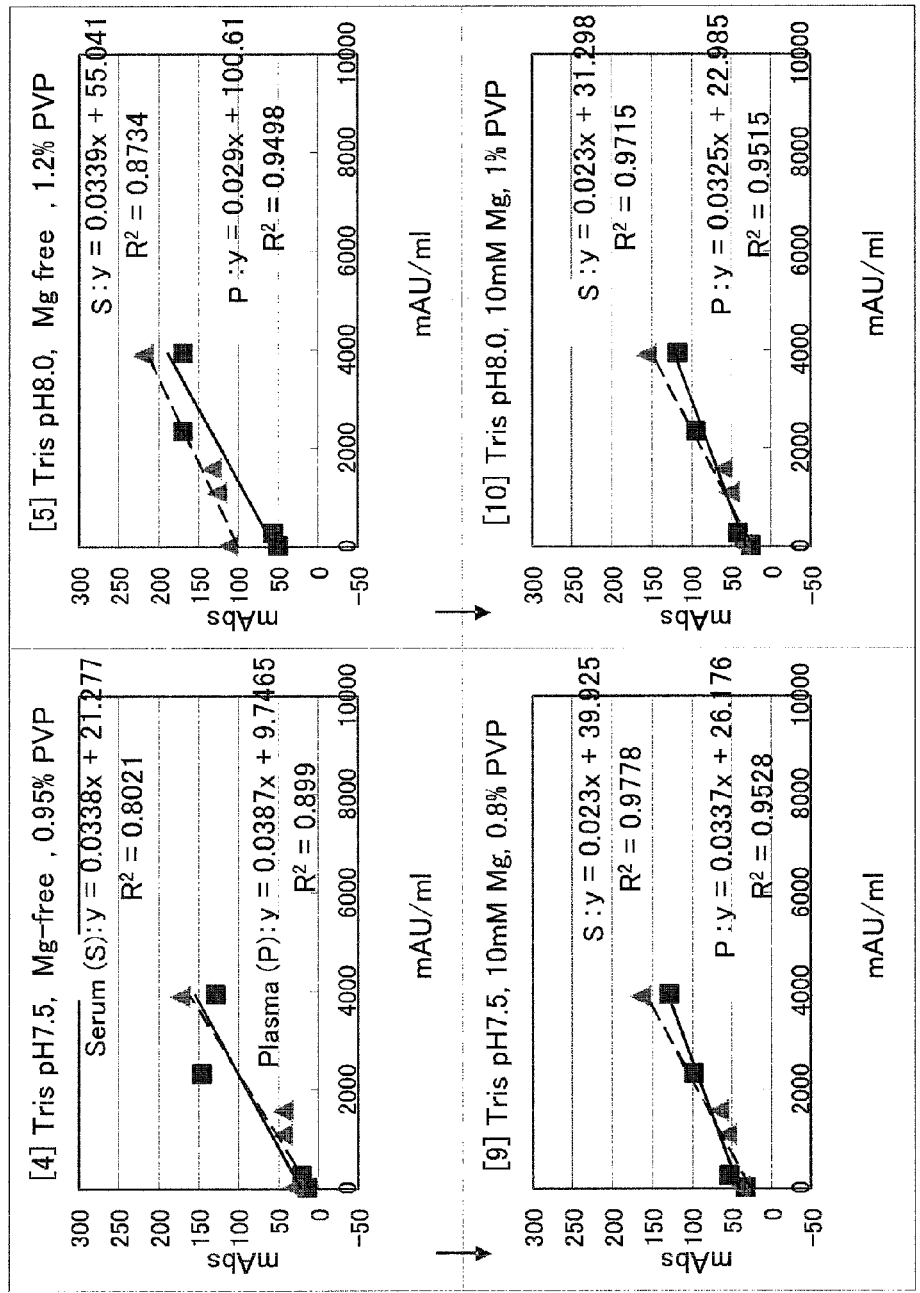
[FIG. 3-2]

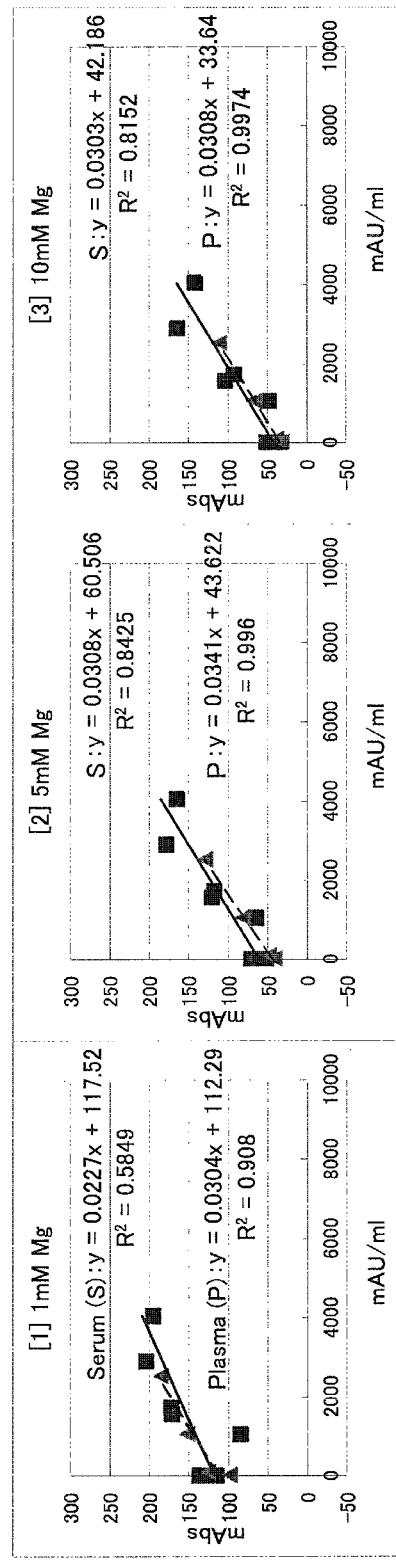
[FIG. 4]

METHOD OF INHIBITING NONSPECIFIC REACTION IN PIVKA-II ASSAY REAGENT

TECHNICAL FIELD

The present invention relates to an immunoassay of PIVKA-II, a PIVKA-II assay reagent, and a PIVKA-II assay kit.

BACKGROUND ART

PIVKA-II refers to a protein classified as prothrombin, which is the blood coagulation factor II, without coagulation factor activity, and is also referred to as abnormal prothrombin. Prothrombin is synthesized in liver and the generation process requires conversion of glutamic acid (Glu) residues into γ-carboxyglutamic acid (Gla) residues by vitamin K-dependent γ-glutamyl carboxylase. Although 10 Gla residues are present near the N-terminus of normal prothrombin, PIVKA-II has all or a portion of 10 residues not converted into Gla and remaining as Glu residues. PIVKA-II was initially found in the blood of vitamin K deficient or vitamin K antagonist-treated patients. Since the blood concentration increases in association with hepatoma, PIVKA-II is recently measured as a tumor marker of hepatoma. PIVKA-II is an abbreviation of protein induced by Vitamin K absence or antagonists-II and is also referred to as des-γ-carboxy prothrombin (DCP) (References: Weitz, I. C., and Liebman, H. A., (1993) *Hepatology* 18, 990-997; Suzuki M, Shiraha H, Fujikawa T, Takaoka N, Ueda N, Nakanishi Y, Koike K, Takaki A, Shiratori Y, *J Biol Chem*, 2005 Feb. 25; 280 (8), 6409-15; A. Nakao, A. Virji, Y. Iwaki, B. Carr, S. Iwatsuki, and E. Starzl, *Hepatogastroenterology*, 1991 October, 38(5), 450-453).

As methods for specifically measuring PIVKA-II in a sample, presently known are a method of separating prothrombin and PIVKA-II by using HPLC (*Anal Biochem*, 1984 February; 137(1), 227-9), a method of separating prothrombin and PIVKA-II with polyacrylamide gel-affinity electrophoresis using calcium lactate (Non-Patent Literature 1), an ELISA-based method using an antibody specifically reactive with PIVKA-II (DCP) (Non-Patent Literature 2), etc.

In the method of Non-Patent Literature 1, calcium lactate is used at the time of electrophoresis and this is intended to generate a difference in electrophoretic mobility between normal prothrombin and PIVKA-II due to the presence of calcium-binding capacity of the Gla residues so as to separate the both.

In Non-Patent Literature 2, PIVKA-II is measured by using an antibody (C4B6) specifically binding to PIVKA-II only under the presence of calcium ions. However, only the C4B6 antibody is reported as an anti-PIVKA-II antibody requiring the presence of calcium ions for specifically measuring PIVKA-II until now. Therefore, the addition of calcium is usually not required for using an antibody specifically reactive with PIVKA-II (DCP) in a measuring method of PIVKA-II.

The current mainstream of methods for specifically measuring PIVKA-II in a sample is a method based on EIA (enzyme immunoassay), RIA (radioimmunoassay), or ELISA (enzyme-linked immunoassay) of measuring through a two-step sandwich method using a monoclonal antibody specifically reactive with PIVKA-II (DCP) and an anti-prothrombin polyclonal antibody (e.g., JP H05-43357 A (Translation of PCT Application) and JP H09-43237 A).

Calcium is not used in the measuring methods of JP H05-43357 A (Translation of PCT Application), JP H09-43237 A, and International Publication Pamphlet No. WO 2010/104815 based on ELISA and it is generally considered that calcium ions are unnecessary for measurement of PIVKA-II.

Patent Literature 1 is an example of measuring PIVKA-II by utilizing agglutination of carrier particles. A summary of the technique of Patent Literature 1 is as follows. First, a sample is added to magnetic particles carrying a PIVKA-II specific antibody to bind PIVKA-II in the sample to the antibody. At this point, normal prothrombin in the sample is not bound to the magnetic particles. The magnetic particles are trapped by a magnet and washed to remove normal prothrombin. Fluorescent-labeled particles carrying an anti-prothrombin antibody reactive with both PIVKA-II and normal prothrombin is then added to the magnetic particles. As a result, a sandwich structure is formed with the magnetic particles and the fluorescent-labeled particles bound through the two antibodies to PIVKA-II. The sandwich structure is trapped by a magnet and washed to remove the free fluorescent-labeled particles. Lastly, the sandwich structure is alkali-treated to dissociate the fluorescent-labeled particles from PIVKA-II to measure fluorescence intensity. The fluorescence intensity is proportional to PIVKA-II concentration in the sample. As described above, the method described in Patent Literature 1 is a heterogeneous measuring method having the steps of B/F separation/washing and employs as the detection principle the measurement of fluorescence intensity derived from the fluorescent-labeled particles rather than utilizing as the detection principle the optical measurement of agglutination of the carrier particles itself.

Patent Literature 2 teaches in Examples a basic technique of latex agglutination test employing as the detection principle the optical measurement of agglutination of carrier particles itself in a homogeneous system without the need of the steps of B/F separation/washing. The document teaches "a highly-sensitive immunoassay method characterized in that two different types of monoclonal antibodies to human CEA are carried by two types of latex carriers and are reacted with human CEA in a water solvent to selectively agglutinate the conjugates of the latex carriers and human CEA, wherein the two types of latex particles have average particle diameters different from each other and within a range of 0.05 to 0.500 μm and said monoclonal antibodies are carried by the respective latex particles".

CITATION LIST

Patent Literature

Patent Literature 1: Japanese Laid-Open Patent Publication No. 2003-75438 (JP 2003-75438 A)
Patent Literature 2: Japanese Laid-Open Patent Publication No. H10-123137 (JP 10-123137 A)
Patent Literature 3: Japanese Unexamined Patent Application Publication (Translation of PCT Application) No. H05-43357 (JP H05-43357 B)

Non Patent Literature

Non Patent Literature 1: Des-gamma-carboxyprothrombin detection by immunoblotting after polyacrylamide gel affinoelectrophoresis in human plasmas. Belle M, Hanss M, Guillaumont M, Leclercq M, Guinet R. *Electrophoresis* 1991 April; 12(4): 294-7.

Non Patent Literature 2: Production of a new monoclonal antibody specific to human des-gamma-carboxyprothrombin in the presence of calcium ions. Application to the development of a sensitive ELISA-test. Belle M, Brebant R, Guinet R, Leclercq M. J *Immunoassay.* 1995 May; 16(2): 213-29.

SUMMARY OF INVENTION

Technical Problem

Although the method using HPLC and the ELISA-based method are well-established and highly-reliable measuring methods as a method for specifically measuring PIVKA-II in a sample, the methods still have problems of the lack of simplicity such as lengthy measurement time per analyte and necessity to wash unreacted substances.

The technique taught in Patent Literature 2 is very excellent in terms of simplicity. When this technique is used, human CEA concentration in a sample can be measured by adding the sample to two types of latex particles carrying two different types of monoclonal antibodies to human CEA and directly measuring a change in absorbance associated with agglutination of the latex particles.

To measure PIVKA-II, if at least one of the monoclonal antibodies has a property of specifically binding to PIVKA-II, specificity of a measurement system can be ensured and, therefore, the other monoclonal antibody does not have to have the property of specifically binding to PIVKA-II as long as it binds to prothrombin (either normal or abnormal). If at least either one of the monoclonal antibodies is specific to PIVKA-II, the presence of calcium ions is normally not necessary in the measuring method of PIVKA-II.

The present inventors attempted to develop a simple and highly-reliable PIVKA-II measuring method employing the principle of a carrier particle-agglutination test based on the technique of Patent Literature 2. It is known that, in an immunoassay such as a latex immune agglutination method, a nonspecific reaction due to interference by rheumatoid factor and a heterophilic antibody (e.g., an anti-mouse immunoglobulin antibody (HAMA) and anti-goat immunoglobulin antibody (HAGA)) can cause a problem depending on the sample to be measured. To inhibit these interferences, a method of removing the Fc site of the antibody to be bound to latex particles and a method of adding an anti-HAMA agent (Heteroblock manufactured by OMEGA Biologicals and HBR manufactured by Scantibodies Lab) etc., to the solution for immune reaction are generally known.

However, the study of the present inventors revealed the occurrence of nonspecific agglutination, in an agglutination test using two types of latex particles respectively carrying two types of monoclonal antibodies for measuring PIVKA-II, that cannot be inhibited by the removal of the Fc site of antibody and by the use of anti-HAMA agents: one type of the monoclonal antibodies having a property of specifically binding to PIVKA-II and the other type of the monoclonal antibodies having a property of specifically binding to prothrombin (normal prothrombin and PIVKA-II).

Therefore, a problem to be solved by the present invention is to inhibit nonspecific agglutination reactions in an agglutination test using two types of monoclonal antibodies for measuring PIVKA-II and two types of carrier particles carrying these monoclonal antibodies.

Solution to Problem

The inventors have found that, in an agglutination test using two types of carrier particles respectively carrying two types of monoclonal antibodies for measuring PIVKA-II, i.e., one type of the monoclonal antibodies having a property of specifically binding to PIVKA-II and the other type of the monoclonal antibodies having a property of specifically binding to prothrombin, the addition of divalent metal ions to reaction solution can inhibit the nonspecific agglutination reaction.

The invention completed by the present inventors based on the above findings includes the following.

(1) A method of measuring concentration of PIVKA-II in a biological sample comprising the steps of:

bringing first carrier particles to which a first monoclonal antibody is immobilized and second carrier particles to which a second monoclonal antibody is immobilized into contact with the biological sample under the presence of divalent metal ions; and optically measuring agglutination of said first carrier particles and said second carrier particles, wherein one of the first and second monoclonal antibodies is an antibody specifically binding to PIVKA-II while the other is an antibody specifically binding to prothrombin, wherein the both antibodies bind to different epitopes, and wherein the divalent metal ions are ions of one or more selected from the group consisting of $Be^{2+}$, $Mg^{2+}$, $Ca^{2+}$, $Sr^{2+}$, $Ba^{2+}$, and $Ra^{2+}$ and are not derived from the biological sample.

(2) The method according to item (1), wherein the divalent metal ions are ions of one or more selected from the group consisting of $Mg^{2+}$ and $Ca^{2+}$.

(3) The method according to item (1) or (2), wherein the first or second carrier particles are latex particles.

(4) The method according to item (1), wherein the step of bringing into contact and the step of measuring are performed in the same reaction solution or in the same reaction vessel.

(5) A reagent for measuring concentration of PIVKA-II through an agglutination reaction comprising:

first carrier particles to which a first monoclonal antibody is immobilized;

second carrier particles to which a second monoclonal antibody is immobilized; and divalent metal ions, wherein one of the first and second monoclonal antibodies is an antibody specifically binding to PIVKA-II while the other is an antibody specifically binding to prothrombin, wherein the both antibodies bind to different epitopes, and wherein the divalent metal ions are ions of one or more selected from the group consisting of $Be^{2+}$, $Mg^{2+}$, $Ca^{2+}$, $Sr^{2+}$, $Ba^{2+}$, and $Ra^{2+}$.

(6) The reagent according to item (5), wherein neither the first carrier particles nor the second carrier particles are fluorescent carrier particles.

(7) A kit of parts for measuring concentration of PIVKA-II through an agglutination reaction comprising:

a first reagent containing divalent metal ions; and a second reagent containing first carrier particles to which a first monoclonal antibody is immobilized and second carrier particles to which a second monoclonal antibody is immobilized, wherein one of the first and second monoclonal antibodies is an antibody specifically binding to PIVKA-II while the other is an antibody specifically binding to prothrombin, wherein the both antibodies bind to different epitopes, and wherein the divalent metal ions are ions of one or more selected from the group consisting of $Be^{2+}$, $Mg^{2+}$, $Ca^{2+}$, $Sr^{2+}$, $Ba^{2+}$, and $Ra^{2+}$.

(8) The kit of parts according to item (7), wherein neither the first carrier particles nor the second carrier particles are fluorescent carrier particles.

Advantageous Effects of Invention

By using the present invention, simple and highly-reliable PIVKA-II measurement can be performed.

BRIEF DESCRIPTION OF DRAWINGS

FIG. 1 shows the effect of addition of calcium ions on correlation between concentration of PIVKA-II in a sample and the absorbance.

FIG. 2 shows the effect of addition of magnesium ions on correlation between concentration of PIVKA-II in a sample and the absorbance.

FIGS. 3-1 and 3-2 show the effect of addition of magnesium ions when pH is varied.

FIG. 4 shows the effect of addition of magnesium ions on correlation between concentration of PIVKA-II in a sample and the absorbance.

DESCRIPTION OF EMBODIMENTS

Biological sample: As used herein, a "biological sample" refers to a biological sample of a mammal, preferably, a human. A biological sample may be any sample in which prothrombin may exist (e.g., those derived from a tissue expressing prothrombin or body fluid through which prothrombin circulates) and is preferably blood, serum, plasma, or lymph fluid.

PIVKA-II: As used herein, "PIVKA-II" refers to PIVKA-II of a mammal, preferably, a human.

Prothrombin: In this description, both normal prothrombin and abnormal prothrombin are collectively referred to as "prothrombin". As used herein, "abnormal prothrombin" refers to PIVKA-II, and "normal prothrombin" refers to prothrombin other than PIVKA-II.

Monoclonal antibody: As used herein, a "monoclonal antibody" may refer to an antibody itself or may refer to a fragment such as Fab fragment and $F(ab')_2$ fragment having binding activity to an antigen. The monoclonal antibody may be acquired by any acquisition methods: it may be an antibody acquired by classical immunization of an antigen to a nonhuman animal or an antibody acquired by a gene recombination technique or a gene immunization method. The antibody may bind to a known labeling substance such as peroxidase, alkaline phosphatase, biotin, colloidal metal, and FITC. If required, a "reagent containing an antibody or antibodies" may also contain a salt, a buffering agent, a preservative, a surfactant, a reducing agent, and a cryoprotectant. In the present invention, it is necessary to use two types of monoclonal antibodies; however, this is not intended to exclude the use of three or more types. It is also not excluded that the two types of monoclonal antibodies, which are immobilized and used on the carrier particles, are further added in a free state without immobilization to the carrier particles.

Immobilization: As used herein, the term "immobilization", "solid-phased", and "sensitization" are used in the same meaning.

Carrier particles: Carrier particles (insoluble carriers) used in the present invention include, for example, organic polymer powders, inorganic material powders, microorganisms, hemocytes, and cell debris.

The organic polymer powders include, for example, natural polymer powders such as insoluble agarose, cellulose, and insoluble dextran, and synthetic polymer powders such as polystyrene, styrene-styrene sulfonate copolymer, acrylonitrile-butadiene-styrene copolymer, vinyl chloride-acrylic acid ester copolymer, and vinyl acetate-acrylic acid ester copolymer, and particularly, latex particles acquired by uniformly suspending synthetic polymer powders are preferable.

The inorganic material powders include, for example, metal pieces of gold, titanium, iron, nickel, etc., silica, alumina, and carbon powders.

The average particle diameter of the insoluble carriers is typically 0.05 to 1.0 μm. The particle diameters and the materials of the two types of carrier particles carrying two types of monoclonal antibodies may be the same or different.

Divalent metal ions: As used herein, "divalent metal ions" refer to $Be^{2+}$, $Mg^{2+}$, $Ca^{2+}$, $Sr^{2+}$, $Ba^{2+}$, or $Ra^{2+}$. Among these, $Ca^{2+}$ or $Mg^{2+}$ is preferable, and $Mg^{2+}$ is more preferable. Concentration of $Be^{2+}$, $Mg^{2+}$, $Ca^{2+}$, $Sr^{2+}$, $Ba^{2+}$, or $Ra^{2+}$ is preferably 1 to 50 mmol/L, 2 to 50 mmol/L, 3 to 50 mmol/L, 5 to 50 mmol/L, 7 to 50 mmol/L, or 10 to 50 mmol/L, more preferably 2 to 30 mmol/L, 3 to 30 mmol/L, 5 to 30 mmol/L, 7 to 30 mmol/L, or 10 to 30 mmol/L, further preferably 3 to 20 mmol/L, 5 to 20 mmol/L, 7 to 20 mmol/L, or 10 to 20 mmol/L. The divalent metal ions of the present invention are not derived from biological samples to be measured for PIVKA-II. Above concentrations indicate the concentration at the time of agglutination reaction of PIVKA-II and carrier particles to which antibodies are immobilized. The divalent metal ions can easily obtained and used as halides such as $MgCl_2$ and $CaCl_2$ or in the forms of inorganic acid salts such as $MgSO_4$ and $CaSO_4$, alkali salts such as $Mg(OH)_2$ and $Ca(OH)_2$, and organic acid salts such as $MgC_2O_4$ and $CaC_2O_4$.

Bringing into contact: As used herein, when carrier particles are "brought into contact" with a biological sample, this means that the carrier particles and the biological sample are mixed in the form of solid, aqueous solution, or suspension.

Agglutination: As used herein, "agglutination" means that multiple carrier particles of the same type or different types to which antibodies are immobilized are bound to each other via binding between PIVKA-II and the antibodies. This agglutination causes a change in the intensity, wavelength, or phase of transmitted or scattered light when light is applied to a suspension containing the carrier particles.

Optically measuring: A method for optical measurement is preferably a method using a spectrophotometer or a light scattering photometer.

Optically measuring agglutination: As used herein, "optically measuring agglutination" of particles means that measurement is performed while agglutination of a plurality of types of particles is continuing. Therefore, "optically measuring agglutination" does not mean that one type of particles is separated from the other particles and optically measured after particles have once agglutinated.

Specifically binding to PIVKA-II: As used herein, when an antibody "specifically binds to PIVKA-II", this means that the antibody binds to PIVKA-II and does not bind to a substance other than PIVKA-II and particularly means that the antibody does not bind to normal prothrombin.

Specifically binding to prothrombin: As used herein, when an antibody "specifically binds to prothrombin", this means that the antibody binds to at least one of normal prothrombin and PIVKA-II and does not bind to a substance other than normal prothrombin and PIVKA-II.

In the above description, "does not bind" does not mean complete absence of binding, and an antibody causing some nonspecific binding is usable in the present invention unless an error more than acceptable level is generated when concentration of PIVKA-II is measured.

Binding to different epitopes: When a plurality of monoclonal antibodies used in the method, reagent, or kit of the present invention "bind to different epitopes", this means that the respective antibodies recognize different sites on PIVKA-II. This is because the plurality of monoclonal antibodies should not compete with each other when binding to PIVKA-II.

Nonspecific agglutination: As used herein, "nonspecific agglutination" or "nonspecific agglutination reaction" refers to aggregation other than specific agglutination. It is practically difficult to directly distinguish the difference between specific agglutination and nonspecific agglutination and, if a measurement value is away from an expected value in optical measurement, it is considered that "nonspecific agglutination" is observed.

A reagent for measuring concentration of PIVKA-II through an agglutination reaction of the present invention includes the following constituent elements:

Element 1: first carrier particles to which a first monoclonal antibody is immobilized;

Element 2: second carrier particles to which a second monoclonal antibody is immobilized; and Element 3: divalent metal ions, wherein one of the first and second monoclonal antibodies is an antibody specifically binding to PIVKA-II while the other is an antibody specifically binding to prothrombin, wherein the both antibodies bind to different epitopes, and wherein the divalent metal ions are ions of one or more selected from the group consisting of $Be^{2+}$, $Mg^{2+}$, $Ca^{2+}$, $Sr^{2+}$, $Ba^{2+}$, and $Ra^{2+}$.

With regard to the reagent of the present invention for measuring a target substance in a sample through agglutination reaction using carrier particles to which antibodies are immobilized, the elements 1 to 3 may be formed as respective independent constituent reagents or two or more of the elements may be combined as needed to form a constituent reagent. In many cases, the reagent is configured in the form of a first reagent and a second reagent. A specific example in the case of configuration in the form of the first reagent and the second reagent can be a reagent (kit) made up of the first reagent containing the element 3 and the second reagent containing the elements 1 and 2, which is preferred for the present invention. Above configuration will further be described. The first reagent adjusts (diluting) concentrations of a target substance and impurities and adjusts pH and ion intensity at the time of agglutination reaction in the reaction system. The second reagent causes an agglutination reaction by the carrier particles to which antibodies are immobilized after a measurement environment is created by the first reagent. The first reagent or the second reagent can contain commonly used pH buffering agents, salts, proteins, peptides, surfactants, reaction accelerators (sensitizers), nonspecific reaction-inhibiting agents, preservation stabilizers, preservatives, etc., as needed along with the elements 1 to 3 to the extent that the agglutination reaction by the carrier particles to which antibodies are immobilized is not blocked. Preferred pH and salt concentration at the time of the agglutination reaction can be, for example, pH 5 to 9 and 5 to 500 mmol/L, respectively, and the pH and salt concentration can be achieved by a combination of the first reagent and the second reagent. In the description, the first reagent and the second reagent are named based on the order of contact with a biological sample and may be named in a different manner. For example, the first reagent can be referred to as a diluting solution and the second reagent can be referred to as a latex reagent. The explanation above is not intended to limit the present invention and, for example, the elements 1 to 3 may appropriately be contained in both the first and second reagents or only in the second reagent. Those skilled in the art will easily understand that such appropriate modifications are possible.

A kit of parts for measuring concentration of PIVKA-II through an agglutination reaction of the present invention includes the following constituent elements:

Element A: a first reagent containing divalent metal ions;

Element B: a second reagent containing first carrier particles to which a first monoclonal antibody is immobilized and second carrier particles to which a second monoclonal antibody is immobilized; and, optionally, Element C: a document describing that the first reagent and the second reagent are combined for measuring the concentration of PIVKA-II, wherein one of the first and second monoclonal antibodies is an antibody specifically binding to PIVKA-II while the other is an antibody specifically binding to prothrombin, wherein the both antibodies bind to different epitopes, and wherein the divalent metal ions are ions of one or more selected from the group consisting of $Be^{2+}$, $Mg^{2+}$, $Ca^{2+}$, $Sr^{2+}$, $Ba^{2+}$, and $Ra^{2+}$.

The kit of the present invention refers to a form of the reagent when the elements C explicitly/implicitly describes in an understandable manner that the element A and the element B are combined to be used for the measurement of PIVKA-II. Therefore, obviously not only when the element A, the element B, and the element C are packed in the same package or when the first reagent and the second reagent are concurrently distributed, but also even when each of the first and second reagents is independently/separately distributed, the kit of the present invention may be formed as long as the elements C has such a description. The document of the element C may have any name and form such as an attached document, a pamphlet, and a catalogue and may be in writing or recorded in an electronic medium.

The kit may also include a substance for concentration calibration (so-called calibrator), a sample with known PIVKA-II concentration for precision control (so-called control), etc., for calculating the PIVKA-II concentration in a biological sample.

EXAMPLES

Experimental Materials and Methods

<Monoclonal Antibody (Anti-PIVKA-II Antibody): MU-3 Antibody>

(1) Production Method

For an anti-PIVKA-II monoclonal antibody (MU-3 antibody), an antibody produced by the very method described in the first example of Patent Literature 3 was used.

The antibody production method described in the first example of Patent Literature 3 will hereinafter be cited in a partially abbreviated manner.

"(B) $BaSO_4$ and $BaCO_3$ were added to the plasma of warfarin administered patients at a ratio of 100 mg/mL each and stirred for 120 minutes to adsorb and remove normal prothrombin and the plasma was added to DE-52 cellulose for ion exchange, applied to the affinity column using a monoclonal antibody against a portion common to both normal prothrombin and PIVKA-II, eluted with 4M guanidine hydrochloride, dialyzed, and concentrated to purify PIVKA-II. Acquired PIVKA-II (50 μg) was intraperitoneally administered to BALB/C mice (female, four weeks old) along with the same volume of Freund's complete adjuvant; after two weeks, PIVKA-II (15 μg) was further administered into the tail vein and spleen cells were excised three days later; and the cells were fused with the tumor cell strain P3U1. The cell fusion was performed by the method of Watanabe et al. using polyethylene glycol 4,000. Cloning was then performed three times with a limiting dilution method using a 96-well microplate. The assay for the cloning was performed by using decarboxylated human prothrombin of (A) above and, eventually, native PIVKA-II. Identification symbols . . . , MU-3, . . . were applied to respective cell lines of antibody-producing hybridomas established by the cloning . . . . The monoclonal anti-PIVKA-II antibody was acquired from the cell line MU-3 in the usual manner."

As described in the citation, the screening of anti-PIVKA-II antibody produced by hybridomas acquired by immunization with PIVKA-II was performed through the assay for cloning of antibody-producing hybridomas using decarboxylated human prothrombin and, eventually, native PIVKA-II.

It has been identified and confirmed that the epitopic site of the MU-3 antibody is a "decarboxyl-peptide site at 13th to 23th positions of the amino acid sequence of prothrombin" as a result of a detailed study of the binding ability using peptide fragments of various lengths synthesized based on the Gla region amino acid sequence of PIVKA-II (JP H07-20127 A). Therefore, in addition to native PIVKA-II and decarboxylated human prothrombin in Patent Literature 3, peptide fragments of various lengths synthesized based on the Gla region amino acid sequence of PIVKA-II described in JP H07-20127 A etc., can appropriately be combined to compare and confirm the ability of an antibody to bind to PIVKA-II and substances other than PIVKA-II for the screening of an anti-PIVKA-II antibody. As a result, a new anti-PIVKA-II antibody other than MU-3 antibody can further be acquired. Patent Literature 3 (JP H05-43357 A (Translation of PCT Application)) and JP H07-20127 A are herein incorporated by reference in its entirety.

Anti-PIVKA-II antibodies other than MU-3 are also known. For example, 2G4 antibody described in JP H09-43237 A and an antibody the epitopic site of which is a decarboxyl-peptide site at 13th to 27th positions of the amino acid sequence of PIVKA-II as described in International Publication Pamphlet No. WO 2010/104815 are considered to be usable as the anti-PIVKA-II antibody of the present invention.

<Monoclonal Antibodies (Anti-Prothrombin Antibodies): 24209-Antibody, 24219-Antibody>

(1) Production Method i) Preparation of Hybridoma

PIVKA-II (1 mg/mL) purified from Coumadin plasma (manufactured by UNIGLOBE RESEARCH CORPORATION) and Freund's complete adjuvant (manufactured by GIBCO) were mixed one-to-one and emulsified and were subcutaneously administered to eight-week old female BALB/C mice (produced by Charles River Laboratories Japan) at a dose of 50 μg/100 μL four times at two-week intervals and, after three days from the final immunization, the spleen was excised. The spleen cells acquired from the excised spleen and myeloma cells SP2/O—Ag14 were mixed at a ratio of 10 to 1 for cell fusion in the presence of 50 wt % polyethylene glycol 1540 (manufactured by Wako Pure Chemical Industries). The fused cells were suspended in HAT medium at $2.5 \times 10^6$ cells/mL with respect to spleen cells and dispensed by 0.2 mL to 96-well culture plates (manufactured by CORNING). The fused cells were cultured at 37° C. in 5 vol % $CO_2$ incubator. After about two weeks, the culture supernatant of wells with growing hybridomas was evaluated in accordance with the ELISA method described below to select hybridomas producing an antibody reactive with PIVKA-II.

Specifically, 5 ng of the purified PIVKA-II was first solid-phased on a microplate (manufactured by NUNC). After reacted with the culture supernatants, the microplate was reacted with a peroxidase-labeled anti-mouse IgG goat antibody. Peroxidase substrate solution containing ortho-phenylenediamine (manufactured by Tokyo Chemical Industry) was added for coloring, which was stopped by adding 1.5 N sulfuric acid. The absorbance was measured by a microplate reader at a wavelength of 492 nm to acquire hybridoma 09 and hybridoma 19 producing antibodies specifically reactive with prothrombin.

ii) Preparation of Monoclonal Antibody

The 24209 monoclonal antibody (24209-antibody) and the 24219 monoclonal antibody (24219-antibody) were prepared from the hybridoma 09 and hybridoma 19, respectively, by the following method.

The hybridoma was intraperitoneally administered in an amount of $0.5 \times 10^6$ cells to 12-week-old female BALB/c mice preliminarily intraperitoneally injected with 0.5 mL of pristane two weeks before. The ascites were collected after about 14 days, and supernatant was acquired by centrifugation. The supernatant was mixed with the same amount of adsorption buffer solution (3 mol/L NaCl-1.5 mol/L Glycine-NaOH, pH 8.5) and then filtrated. The filtrate was passed through a protein A column (HiTrap rProteinA FF manufactured by GE Healthcare Japan) equilibrated with the adsorption buffer solution to adsorb antibodies with the column. The monoclonal antibodies were eluted with 0.1 mol/L citrate buffer solution (pH 3.0) and purified.

(2) Accession Number

The hybridomas 09 and 19 were deposited at International Patent Organism Depositary, National Institute of Advanced Industrial Science and Technology (Tsukuba Central 6, 1-1-1 Higashi, Tsukuba, Ibaraki, Japan) (date of receipt: May 11, 2011) under the accession numbers FERM BP-11381 and FERM BP-11382, respectively.

<Production of Latex Particles>

A glass reaction container (capacity: 2 L) equipped with a stirring machine, a reflux condenser, a temperature detector, a nitrogen introduction tube, and a jacket was filled with 1,100 g of distilled water, 200 g of styrene, 0.2 g of sodium styrene sulfonate, and an aqueous solution of 1.5 g of potassium persuphate dissolved in 50 g of distilled water, and after the inside of the container was replaced with nitrogen gas, polymerization was performed for 48 hours while stirring at 70° C.

After the end of polymerization, the solution was filtrated with filter paper to extract latex particles. The particle diameter of the acquired latex particles were measured by using a transmission electron microscope apparatus (manufactured by JEOL Ltd., "model JEM-1010") for imaging the latex particles at a magnification of 10,000 times and performing the image analysis of 100 or more particles. The average particle diameter was 0.3 μm. In this description, the latex particles may be denoted by Lx.

<Preparation of Antibody-Sensitized Latex Particles> i) Preparation of 24209-Antibody-Sensitized Latex Particle Solution

To 1 mL of 1.0 wt % latex particle solution (5 mmol/L Tris-hydrochloric acid buffer solution (hereinafter, referred to as Tris-HCl), pH 7.5) having the average particle diameter of 0.3 μm as described above, 1 mL of 24209-antibody solution diluted to 0.60 mg/mL with 5 mmol/L Tris-HCl (pH 7.5) was added and stirred at 4° C. for two hours. Subsequently, 1 mL of 5 mmol/L Tris-HCl (pH 7.5) containing 0.5 wt % BSA was added and stirred at 4° C. for one hour. Lastly, after the solution was centrifuged and supernatant was removed, the precipitate was resuspended in 5 mmol/L Tris-HCl (pH 7.5) to produce a 24209-antibody-sensitized latex particle solution.

ii) Preparation of 24219-Antibody-Sensitized Latex Particle Solution

The latex particles having the average particle diameter of 0.3 μm and the 24219-antibody were used for producing a 24219-antibody-sensitized latex particle solution in the same method as described above.

iii) Preparation of MU3-Antibody-Sensitized Latex Particles

The latex particles having the average particle diameter of 0.3 μm and the MU3-antibody were used for producing an MU3-antibody-sensitized latex particle solution in the same method as described above.

<Preparation of First Reagent>

The first reagent was acquired by preparing 100 mmol/L Bis-Tris (pH 6.0) solution containing 300 mmol/L sodium chloride, 0.2 wt % BSA, 200 μg/mL Heteroblock (manufactured by OMEGA Biologicals), and 0.9 wt % of polyvinyl pyrrolidone K-90 (hereinafter, PVP).

In this description, the first reagent may be referred to as R1 for convenience.

<Preparation of Second Reagent>

The second reagent was acquired by mixing the MU3-antibody-sensitized latex particle solution with either the 24209-antibody-sensitized latex particle solution or the 24219-antibody-sensitized latex particle solution in equal amounts (see the examples) and diluting the solution with 5 mmol/L Tris-HCl (pH 7.5) to absorbance of 6.0 Abs at a wavelength of 600 nm.

In this description, this mixed solution (second reagent) may be referred to as R2 for convenience.

<Sample>

PIVKA-II concentrations in serum and plasma were measured by using Picolumi (registered trademark) PIVKA-II (manufactured by Sanko Junyaku Co., Ltd.). The measurement values of PIVKA-II were compared with measurement values from the measuring method of the present invention. Picolumi (registered trademark) PIVKA-II is widely distributed as an in vitro diagnostic reagent and, because of the principle of two-step electrochemiluminescence immunoassay, the reagent rarely causes nonspecific reaction.

<Measuring Method>

The first and second reagents were combined and samples were measured by using a Hitachi 7170 Automated Analyzer. Specifically, after 150 μL of the first reagent was added to 10 μL of the sample and stirred, temperature was kept at 37° C. for five minutes and 50 μL of the second reagent was added and stirred. Changes in absorbance associated with agglutination formation due to the antibody-sensitized latex particles were then measured for five minutes at a dominant wavelength of 570 nm and a sub-wavelength of 800 nm.

Results and Discussion

Example 1

Ten μL of serum samples containing PIVKA-II at a concentration of 4, 22, 617, 2755, or 6357 mAU/mL were prepared, diluted with 150 μL of R1 containing calcium ions at a concentration from 0 to 50 mmol/L, and kept at a temperature of 37° C. for five minutes. The samples were then mixed with 50 μL of R2 containing the 24219-antibody-sensitized latex particles and the MU3-antibody-sensitized latex particles. The agglutination of the antibody-sensitized latex particles was detected by measuring the absorbance at a dominant wavelength of 570 nm and a sub-wavelength of 800 nm for 5 minutes. Plasma samples containing PIVKA-II at a concentration of 27, 1177, 4063, or 6603 mAU/mL were also prepared for performing the same operation. The compositions of R1 and R2 used in Example 1 are shown in Table 1. To R1, calcium ions were added by the addition of $CaCl_2$. PVP was contained as a sensitizer for the antibody-sensitized latex particles (The same applies to the following).

TABLE 1

| R1 |
| --- |
| 100 mM Bis-Tris pH 6.0 |
| 300 mM NaCl |
| 200 μg/mL Heteroblock |
| 0.9% PVP |
| (the above are common components) |

| | Ca concentration |
| --- | --- |
| 1 | 0 mM |
| 2 | 1 mM |
| 3 | 10 mM |
| 4 | 30 mM |
| 5 | 50 mM |

| R2 |
| --- |
| Equal amounts of the 24219-antibody-sensitized latex particle solution and the MU3-antibody-sensitized latex particle solution were mixed and the mixed solution was diluted with 5 mM Tris-HCl (pH 7.5) to an absorbance of 6.0 Abs at a wavelength of 600 nm. |

When the serum samples were used for the measurement, an $R^2$ value representative of correlation between the concentration of PIVKA-II and the absorbance (a square value of a correlation coefficient) was about 0.52 and nonspecific agglutination reaction was observed in the control, i.e., R1 free of calcium ions. When calcium ions were added at 1 mmol/L to R1, the $R^2$ value was about 0.54 and no improvement in linearity was observed. Surprisingly, when calcium ions were added at 10, 30, or 50 mmol/L to R1, the respective $R^2$ value was about 0.97, about 0.95, or about 0.96 and significant improvement in linearity was observed. See FIG. 1.

When the plasma samples were used for the measurement, the $R^2$ value was from about 0.94 to about 0.98 regardless of whether calcium ions were added to R1 and nonspecific agglutination reaction was not observed.

The same results were obtained when the 24209-antibody-sensitized latex particles were used instead of the 24219-antibody-sensitized latex particles (data not shown).

Example 2

Serum samples containing PIVKA-II at a concentration of 18 (two samples at the same concentration; in duplicate), 1063, 1570, 1729, or 4050 mAU/mL and plasma samples containing PIVKA-II at a concentration of 27, 111, 1065, or 2534 mAU/mL were prepared to conduct the same experiment as Example 1. In Example 2, magnesium ions at a concentration of 10 mmol/L were used instead of calcium ions. For comparison, an experiment using calcium ions at a concentration of 10 mmol/L was also conducted.

When the serum samples were used, the $R^2$ value was about 0.54 comparable with Example 1 and nonspecific agglutination reaction was observed in the control that is R1 free of calcium ions or magnesium ions. When calcium ions were added to R1 at 10 mmol/L, the $R^2$ value was about 0.92 and the improvement in linearity observed in Example 1 was reproduced. When magnesium ions were added to R1 at 10 mmol/L, the $R^2$ value was about 0.87 and significant improvement in linearity was observed as was the case with calcium ions. See FIG. 2.

In the case of using the plasma samples, the $R^2$ value was about 0.89 in the control that is R1 free of calcium ions or magnesium ions; however, when calcium ions or magnesium ions were added at 10 mmol/L, the respective $R^2$ value was about 0.99 or about 1.00 and improvement in linearity was observed. The compositions of R1 and R2 used in Example 2 are shown in Table 2.

TABLE 2

R1

100 mM Bis-Tris pH 6.0
300 mM NaCl
200 µg/mL Heteroblock
0.9% PVP
10 mM $CaCl_2$ or $MgCl_2$

R2

Equal amounts of the 24219-antibody-sensitized latex particle solution and the MU3-antibody-sensitized latex particle solution were mixed and the mixed solution was diluted with 5 mM Tris-HCl (pH 7.5) to an absorbance of 6.0 Abs at a wavelength of 600 nm.

The same results were obtained when the 24209-antibody-sensitized latex particles were used instead of the 24219-antibody-sensitized latex particles (data not shown).

Example 3

Effects on the present invention of pH of a solution for the agglutination reaction of the antibody-sensitized latex particles were tested by changing pH of R1 between pH 6.0 and pH 8.0, and the effect of addition of magnesium ions (10 mmol/L) was examined. In the range of pH 6.0 to 8.0, improvement in linearity was observed due to the addition of magnesium ions to R1 at any pH. See FIG. 3. The compositions of R1 and R2 used in Example 3 are shown in Table 3.

TABLE 3

R1

300 mM NaCl
200 µg/mL Heteroblock
(the above are common components)
Buffers, pH, and $MgCl_2$ and PVP concentrations are as follows.

| | Buffer | pH | $MgCl_2$ | PVP |
|---|---|---|---|---|
| 1 | 100 mM BisTris | 6.0 | — | 1.0% |
| 2 | 100 mM BisTris | 6.5 | — | 1.0% |

TABLE 3-continued

| | | | | |
|---|---|---|---|---|
| 3 | 100 mM BisTris | 7.0 | — | 0.95% |
| 4 | 100 mM Tris | 7.5 | — | 0.95% |
| 5 | 100 mM Tris | 8.0 | — | 1.2% |
| 6 | 100 mM BisTris | 6.0 | 10 mM | 1.1% |
| 7 | 100 mM BisTris | 6.5 | 10 mM | 1.0% |
| 8 | 100 mM BisTris | 7.0 | 10 mM | 0.825% |
| 9 | 100 mM Tris | 7.5 | 10 mM | 0.8% |
| 10 | 100 mM Tris | 8.0 | 10 mM | 1.0% |

R2

Equal amounts of the 24219-antibody-sensitized latex particle solution and the MU3-antibody-sensitized latex particle solution were mixed and the mixed solution was diluted with 5 mM Tris-HCl (pH 7.5) to an absorbance of 6.0 Abs at a wavelength of 600 nm.

The same results were obtained when the 24209-antibody-sensitized latex particles were used instead of the 24219-antibody-sensitized latex particles (data not shown).

Example 4

Serum samples containing PIVKA-II at a concentration of 18 (two samples at the same concentration; in duplicate), 1063, 1570, 1729, 2905, or 4050 mAU/mL and plasma samples containing PIVKA-II at a concentration of 27, 111, 1065, or 2534 mAU/mL were prepared to conduct the same experiment as Example 1. In Example 4, magnesium ions at concentrations of 1, 5, and 10 mmol/L were used instead of calcium ions.

In the case of using the serum samples, when magnesium ions were added to R1 at 1 mmol/L, the $R^2$ value was about 0.58 and the improvement in linearity was not observed in the same way as in Example 2. When magnesium ions were added at 5 mmol/L or 10 mmol/L to R1, the $R^2$ value was about 0.84 or about 0.82 and the improvement in linearity observed in Example 2 was reproduced. See FIG. 4.

In the case of using the plasma samples, when magnesium ions were added at 1 mmol/L, 5 mmol/L, or 10 mmol/L, the respective $R^2$ value was about 0.91, about 1.00, or about 1.00 and improvement in linearity was observed. The compositions of R1 and R2 used in Example 4 are shown in Table 4.

TABLE 4

R1

100 mM Bis-Tris pH 5.7
300 mM NaCl
500 µg/mL Heteroblock
0.9% PVP
1 mM, 5 mM, 10 mM $MgCl_2$

R2

Equal amounts of the 24219-antibody-sensitized latex particle solution and the MU-antibody-sensitized latex particle solution were mixed and the mixed solution was diluted with 5 mM Tris-HCl (pH 7.5) to an absorbance of 6.0 Abs at a wavelength of 600 nm.

The same results were obtained when the 24209-antibody-sensitized latex particles were used instead of the 24219-antibody-sensitized latex particles (data not shown).

INDUSTRIAL APPLICABILITY

The immunoassay of PIVKA-II, the PIVKA-II assay reagent, and the PIVKA-II assay kit of the present invention are utilizable for detection of infantile vitamin K deficiency hemorrhage and hepatoma.

The invention claimed is:

1. A method of measuring concentration of PIVKA-II in a biological sample comprising the steps of:
   bringing first carrier particles to which a first monoclonal antibody is immobilized and second carrier particles to which a second monoclonal antibody is immobilized into contact with the biological sample in which prothrombin may exist under the presence of divalent metal ions; and
   optically measuring agglutination of said first carrier particles and said second carrier particles to determine the concentration of PIVKA-II,
   wherein one of the first and second monoclonal antibodies is an antibody specifically binding to PIVKA-II in the absence of calcium ion while the other is an antibody specifically binding to prothrombin,
   wherein both antibodies bind to different epitopes, and
   wherein the divalent metal ions are ions of one or more selected from the group consisting of $Be^{2+}$, $Mg^{2+}$, $Ca^{2+}$, $Sr^{2+}$, $Ba^{2+}$, and $Ra^{2+}$ and are not derived from the biological sample.

2. The method according to claim 1, wherein the divalent metal ions are ions of one or more selected from the group consisting of $Mg^{2+}$ and $Ca^{2+}$.

3. The method according to claim 1 or 2, wherein the first or second carrier particles are latex particles.

4. The method according to claim 1, wherein the step of bringing into contact and the step of measuring are performed in the same reaction solution or in the same reaction vessel.

5. A reagent for measuring concentration of PIVKA-II through an agglutination reaction comprising:
   first carrier particles to which a first monoclonal antibody is immobilized;
   second carrier particles to which a second monoclonal antibody is immobilized; and
   divalent metal ions,
   wherein one of the first and second monoclonal antibodies is an antibody specifically binding to PIVKA-II in the absence of calcium ion while the other is an antibody specifically binding to prothrombin,
   wherein both antibodies bind to different epitopes, and
   wherein the divalent metal ions are ions of one or more selected from the group consisting of $Be^{2+}$, $Mg^{2+}$, $Ca^{2+}$, $Sr^{2+}$, $Ba^{2+}$, and $Ra^{2+}$.

6. The reagent according to claim 5, wherein neither the first carrier particles nor the second carrier particles are fluorescent carrier particles.

7. A kit of parts for measuring concentration of PIVKA-II through an agglutination reaction comprising:
   a first reagent containing divalent metal ions; and
   a second reagent containing first carrier particles to which a first monoclonal antibody is immobilized and second carrier particles to which a second monoclonal antibody is immobilized,
   wherein one of the first and second monoclonal antibodies is an antibody specifically binding to PIVKA-II in the absence of calcium ion while the other is an antibody specifically binding to prothrombin,
   wherein both antibodies bind to different epitopes, and
   wherein the divalent metal ions are ions of one or more selected from the group consisting of $Be^{2+}$, $Mg^{2+}$, $Ca^{2+}$, $Sr^{2+}$, $Ba^{2+}$, and $Ra^{2+}$.

8. The kit of parts according to claim 7, wherein neither the first carrier particles nor the second carrier particles are fluorescent carrier particles.

9. The method according to claim 1, wherein the biological sample is a sample in which prothrombin exists.

10. The method according to claim 1, wherein the biological sample is blood, serum, plasma, or lymph fluid.

* * * * *